(12) United States Patent
Hannah et al.

(10) Patent No.: US 7,173,165 B2
(45) Date of Patent: Feb. 6, 2007

(54) VARIANTS OF ADP-GLUCOSE PYROPHOSPHORYLASE AFFECTING PHOSPHATE SENSITIVITY AND OTHER PARAMETERS

(75) Inventors: L. Curtis Hannah, Gainesville, FL (US); Joanna Marie-France Cross, Golm (DE)

(73) Assignee: University of Florida Research Foundation, Inc., Gainesville, FL (US)

( * ) Notice: Subject to any disclaimer, the term of this patent is extended or adjusted under 35 U.S.C. 154(b) by 418 days.

(21) Appl. No.: 10/309,398

(22) Filed: Dec. 3, 2002

(65) Prior Publication Data

US 2003/0177533 A1 Sep. 18, 2003

Related U.S. Application Data

(60) Provisional application No. 60/338,083, filed on Dec. 3, 2001.

(51) Int. Cl.
*C12N 15/82* (2006.01)
*C12N 15/29* (2006.01)
*C12N 15/54* (2006.01)
*C12N 15/62* (2006.01)
*C12N 5/04* (2006.01)
*A01H 5/00* (2006.01)
*A01H 1/00* (2006.01)

(52) U.S. Cl. ............... 800/284; 800/276; 800/278; 800/263; 800/287; 800/289; 800/317.2; 800/320.1; 435/69.7; 435/194; 435/320.1; 435/412; 435/417; 435/419; 536/23.2; 536/23.4; 536/23.6

(58) Field of Classification Search ............... 800/278, 800/284, 320.1, 287, 289, 317.2, 260, 275; 435/69.7, 101, 194, 468, 419; 536/23.6, 536/23.4
See application file for complete search history.

(56) References Cited

U.S. PATENT DOCUMENTS

| | | |
|---|---|---|
| 5,498,831 A | 3/1996 | Burgess et al. |
| 5,589,618 A | 12/1996 | Hannah et al. |
| 5,650,557 A | 7/1997 | Hannah et al. |
| 5,712,135 A | 1/1998 | D'Hailuin et al. |
| 5,773,693 A | 6/1998 | Burgess et al. |
| 5,792,290 A | 8/1998 | Huber et al. |
| 5,872,216 A | 2/1999 | Hannah et al. |
| 5,977,437 A | 11/1999 | Villand et al. |
| 6,069,300 A | 5/2000 | Hannah et al. |
| 6,096,945 A | 8/2000 | Burrell et al. |
| 6,184,438 B1 | 2/2001 | Hannah |
| 6,379,968 B1 | 4/2002 | Poulsen |
| 6,403,863 B1 | 6/2002 | Hannah et al. |
| 6,483,011 B1 | 11/2002 | Stemmer et al. |
| 6,486,383 B1 | 11/2002 | Burrell et al. |

2002/0194642 A1 12/2002 Hannah et al.

FOREIGN PATENT DOCUMENTS

| | | |
|---|---|---|
| EP | 455316 A2 | 4/1991 |
| WO | WO 97/42326 A2 | 11/1997 |
| WO | WO 99/07841 | 2/1999 |
| WO | WO 99/58698 A2 | 11/1999 |
| WO | WO 01/64928 A2 | 9/2001 |

OTHER PUBLICATIONS

Hill et al. Biochemical and Biophysical Research Communications 244(2): 573-577 (Mar. 1998).*
Wang et al. The Plant Journal 11(5): 1121-1126 (1997).*
Anderson, J. M. et al. "The Encoded Primary Sequence of a Rice Seed ADP-glucose Pyrophosphorylase Subunit and its Homology to the Bacterial Enzyme" *J. Biological Chemistry*, 1989, pp. 12238-12242. vol. 264, No. 21.
Anderson, J. M. et al. "Molecular Characterization of the Gene Encoding a Rice Endosperm-Specific ADPglucose Pyrophosphorylase Subunit and its Developmental Pattern of Transcription" *Gene*, 1991, pp. 199-205, vol. 97.
Bae, M. M. et al. "Cloning And Characterization Of The *Brittle-2* Gene Of Maize" *Maydica*, 1990, pp. 317-322, vol. 35.
Ballicora et al. "Adenosine 5'-Diphosphate-Glucose Pyrophosphorylase from Potato Tuber" *Plant Physiol.*, 1995, pp. 245-251, vol. 109.
Bhave, M. R. et al. "Identification and Molecular Characterization of *Shrunken-2* cDNA Clones of Maize" *The Plant Cell*, 1990, pp. 581-588, vol. 2.
Copeland, L. et al. "Purification of Spinach Leaf ADPglucose Pyrophosphorylase" *Plant Physiol.*, 1981, pp. 996-1001, vol. 68.
Dickinson, D. B. et al. "Presence of ADP-Glucose Pyrophosphorylase in Shrunken-2 and Brittle-2 Mutants of Maize Endosperm" *Plant Physiol.*, 1969, pp. 1058-1062, vol. 44.
Giroux, M. J. et al. "A Single Gene Mutation That Increases Maize Seed Weight" *Proc. Natl. Acad. Sci. USA*, 1996, pp. 5824-5829, vol. 93.
Govons, S. R. et al., "Isolation of Mutants of *Escherichia coli* B Altered in Their Ability to Synthesize Glycogen" *J. Bacteriol.*, 1969, 97:970-972.
Greene, T. W. et al. "Mutagenesis of the Potato ADPglucose Pyrophosphorylase and Characterization of an Allosteric Mutant Defective in 3-phosphoglycerate Activation" *Proc. Natl Acad. Sci. USA*, 1996, pp. 1509-1513, vol. 93.

(Continued)

*Primary Examiner*—David T. Fox
(74) *Attorney, Agent, or Firm*—Saliwanchik, Lloyd & Saliwanchik

(57) ABSTRACT

The subject invention concerns chimeric AGP subunit proteins and polynucleotides that encode the chimeric proteins. The subject invention provides for mutant AGP enzymes comprising a chimeric subunit of the invention that are less sensitive to inorganic phosphate than wild type AGP enzymes. In one embodiment, the AGP subunit is a small subunit of a plant AGP enzyme. The subject invention also concerns plants comprising a polynucleotide encoding a chimeric AGP subunit protein of the invention. The subject invention also concerns methods for producing a plant comprising a polynucleotide of the present invention. Plants produced according to the invention comprise AGP enzymes that are less sensitive to inorganic phosphate than wild type AGP enzyme.

58 Claims, 3 Drawing Sheets

OTHER PUBLICATIONS

Greene, T. W. et al. "Aspartic Acid 413 Is Important for the Normal Allosteric Functioning of ADP-Glucose Pyrophosphorylase" *Plant Physiol.*, 1996, pp. 1315-1320, vol. 112.

Hannah, L. C. et al. "Characterization of Adenosine Diphosphate Glucose Pyrophosphorylases from Developing Maize Seeds" *Plant Physiol.*, 1975, pp. 297-302, vol. 55.

Hannah, L. C. et al. "Characterization of ADP-Glucose Pyrophosphorylase from *Shrunken-2* and *Brittle-2* Mutants of Maize" *Biochemical Genetics*, 1976, pp. 547-560, vol. 14, Nos. 7/8.

Hannah, L. C. "Starch Synthesis in the Maize Seed" In *Cellular and Molecular Biology of Plant Seed Development*, 1997, pp. 375-405, B.A. Larkins and I.K. Vasil (eds.), Kluwer Academic Publishers, printed in the Netherlands.

Hannah L.C. et al., "Maize Genes Encoding the Small Subunit of ADP-Glucose Pyrophosphorylase", *Plant Physiol.*, 2001, 127:173-183.

Iglesias et al. "Expression of the Potato Tuber ADP-glucose Pyrophosphorylase in *Escherichia coli*" *J. of Biological Chemistry*, 1993, pp. 1081-1086, vol. 268, No. 2.

Lin, Tsan-Piao et al. "A Starch Deficient Mutant of *Arabidopsis thaliana* with Low ADPglucose Pyrophosphorylase Activity Lacks One of the Two Subunits of the Enzyme" *Plant Physiol.*, 1988, pp. 1175-1181, vol. 88.

Morell, M. et al. "Affinity Labeling of the Allosteric Activator Site(s) of Spinach Leaf ADP-glucose Pyrophosphorylase" *J. Biological Chemistry*, 1988, pp. 633-637, vol. 263, No. 2.

Muller-Rober et al. "One of Two Different ADP-glucose Pyrophosphorylase Genes From Potato Responds Strongly to Elevated Levels of Sucrose" *Mol Gen Genet.* 1990, pp. 136-146, vol. 224.

Nakata, P. A. et al. "Comparison of the Primary Sequences of Two Potato Tuber ADP-glucose Pyrophosphorylase Subunits" *Plant Molecular Biology*, 1991, pp. 1089-1093, vol. 17.

Okita, T. W. et al. "The Subunit Structure of Potato Tuber ADPglucose Pyrophosphorylase" *Plant Physiol.*, 1990, pp. 785-790, vol. 93.

Okita, T. W. et al. "Engineering Plant Starches by the Generation of Modified Plant Biosynthetic Enzymes" In *Engineering Crops for Industrial End Uses*, Shewry, P.R., Napier, J.A., and Davis, P., eds., 1996, pp. 1-18, Portland Press Ltd., London.

Olive, M. R. et al. "Isolation and Nucleotide Sequences of cDNA Clones Encoding ADP-glucose Pyrophosphorylase Polypeptides from Wheat Leaf and Endosperm" *J. Molecular Biology*, 1989, pp. 525-538, vol. 12.

Preiss, J. "Bacterial Glycogen Synthesis and Its Regulation" *Ann. Rev. Microbiol.*, 1984, vol. 38, pp. 419-458.

Preiss, J. et al. "Molecular Biology and Regulatory Aspects of Glycogen Biosynthesis in Bacteria" *Progress in Nuc. Acid Res. and Mol Biol.*, 1994, pp. 299-329, vol. 47.

Preiss, J. et al. "Starch Synthesis in Sinks and Sources" In *Photoassimilate distribution in plants and crops: Source-sink relationships*, Zamski, E. and Schaffer, A. A., ed., 1996, pp. 1-63, Marcil Dekker Inc.

Shaw, J. R. et al. "Genomic Nucleotide Sequence of a Wild-Type Shrunkren-2 Allele of *Zea mays*" *Plant Physiol.*, 1992, pp. 1214-1216, vol. 98.

Stark, D. M. et al. "Regulation of the Amount of Starch in Plant Tissues by ADP Glucose Pyrophosphorylase" *Science*, 1992, pp. 287-292, vol. 258.

Tsai, C. Y. et al. "Starch-Deficient Maize Mutant Lacking Adenosine Diphosphate Glucose Pyrophosphorylase Activity" *Science*, 1966, pp. 341-343, vol. 151.

Giroux, et al., "*De novo* synthesis of an intron by the maize transposable element *Dissociation*", *Proc. Natl. Acad. Sci. USA* (1994), pp. 12150-12154, vol. 91.

Badu-Apraku, B., et al., "Effect of Temperature During Grain Filing on Whole Plant and Grain Yield in Maize (*Zea mays* L.)", *Can. J. Plant Sci.* (1983), pp. 357-363, vol. 63.

Broun et al. "Catalytic Plasticity of Fatty Acid Modification Enzymes Underlying Chemical Diversity of Plant Lipids" *Science*, 1998, pp. 131-133, vol. 282.

Burgess et al. "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue" *J. Cell Biol.*, 1990, pp. 2129-2138, vol. 111.

Duvick "Genetic Contributions to Advances in Yield of U.S. Maize" *Maydica*, 1992, pp. 69-79, vol. 37.

Greene et al. "Enhanced Stability of Maize Endosperm ADP-glucose Pyrophosphorylase is Gained Through Mutants that Alter Subunit Interactions" *The Journal of Biological Chemistry*, 1998, pp. 13342-13347, vol. 95.

Sweetlove et al. "Starch Metabolism in Tubers of Transgenic Potato (*Solanum tuberosum*) with Increased ADPglucose pyrophosphorylase" *Biochem. J.*, 1996, pp. 493-498, vol. 320.

Harper, J. L. "Reproduction and Growth" In *Population Biology of Plants*, 1977, pp. 647-675, Academic Press.

Leishman, M. R. et al. "The Evolutionary Ecology of Seed Size" In *Seeds: The Ecology of Regeneration in Plant Communities*, 2d Edition, 2000, ed. M. Fenner, pp. 31-57, CABI Publishing, United Kingdom.

Ainsworth, C. et al. "Adenosine Diphosphate Glucose Pyrophosphorylase Genes in Wheat: Differential Expression and Gene Mapping" *Planta*, 1995, Accession No. S60572.

Chang, Jen-Hu "Corn Yield In Relation To Photoperiod, Night Temperature, And Solar Radiation" *Agricultural Meteorology*, 1981, pp. 253-262, vol. 24.

Charng, Y. Y. et al. "Structure-Function Relationships of Cyanobacterial ADP-glucose Pyrophosphorylase" *J. Biol. Chem.*, 1994, pp. 24107-24113, vol. 269, No. 39.

Cheikh, N. et al. "Heat Stress Effects on Sink Activity of Developing Maize Kernels Grown In Vitro" *Physiologia Plantarium*, 1995, pp. 59-66, vol. 95.

Conroy, J. P. et al. "Influence of Rising Atmospheric $CO_2$ Concentrations and Temperature on Growth, Yield and Grain Quality of Cereal Crops" *Aust. J. Plant Physiol.*, 1994, pp. 741-758, vol. 21.

Duke, E. R. et al. "Effects Of Heat Stress On Enzyme Activities And Transcript Levels In Developing Maize Kernels Grown In Culture" *Environmental and Experimental Botany*, 1996, pp. 199-208, vol. 36, No. 2.

Greene, T. W. et al. "Generation of Up-regulated Allosteric Variants of Potato ADP-glucose Pyrophosphorylase by Reversion Genetics" *Proc. Natl. Acad. Sci. USA*, 1998, pp. 10322-10327, vol. 95.

Hannah, L. C. et al. "Multiple Forms Of Maize Endosperm ADP-Glucose Pyrophosphorylase And Their Control By Shrunken-2 and Brittle-2" *Genetics*, 1980, pp. 961-970, vol. 95.

Hawker, J. S. et al. "High Temperature Affects the Activity of Enzymes in the Committed Pathway of Starch Synthesis in Developing Wheat Endosperm" *Aust. J. Plant Physiol.*, 1993, pp. 197-209, vol. 20.

Jenner, C. F. "Starch Synthesis in the Kernel of Wheat Under High Temperature Conditions" *Aust. J. Plant Physiol.*, 1994, pp. 791-806, vol. 21.

Jenner, C. F. et al. "Thermal Characteristics of Soluble Starch Synthase from Wheat Endosperm" *Aust. J. Plant Physiol.*, 1995, pp. 703-709, vol. 22.

Jensen, L. G. et al. "Transgenic Barley Expressing a Protein-Engineered, Thermostable (1,3-1,4)-β-Glucanase During Germination" *Proc. Natl. Acad. Sci. USA*, 1996, pp. 3487-3491, vol. 93.

Jones, R. J. et al. "Temperature Effects On In Vitro Kernel Development of Maize" *Crop Science*, 1981, pp. 761-766, vol. 21.

Jones, R. J. et al. "Thermal Environment During Endosperm Cell Division And Grain Filling In Maize: Effects On Kernel Growth And Development In Vitro" *Crop Science*, 1984, pp. 133-137, vol. 24.

Keeling, P. L. et al. "Elevated Temperature Reduces Starch Deposition in Wheat Endosperm by Reducing the Activity of Soluble Starch Synthase" *Planta*, 1993, pp. 342-348, vol. 191.

Kim, C. H. et al. "Heat-resistant ADP-glucose Pyrophosphorylase Produced from Thermas Caldophilus sp." *Korea Adv. Inst. Sci. & Technology*, 1998, XP-002127965 (abstract only).

Lafta, A. M. et al. "Effect of High Temperature on Plant Growth and Carbohydrate Metabolism in Potato" *Plant Physiology*, 1995, pp. 637-643, vol. 109.

Laughlin, M. J. et al. "N- and C-terminal Peptide Sequences are Essential for Enzyme Assembly, Allosteric, and/or Catalytic Properties of ADP-glucose Pyrophosphorylase" *The Plant Journal*, 1998, pp. 159-168, vol. 14, No. 2.

Lazar, E. et al. "Transforming Growth Factor α: Mutation of Aspartic Acid 47 and Leucine 48 Results in Different Biological Activities" *Molecular and Cellular Biology*, 1988, pp. 1247-1252, vol. 8, No. 3.

Maniatis, T. et al. "Nuclease Ba/31" In *Enzymes Used in Molecular Cloning, A Laboratory Manual*, 1982, pp. 135-139, Cold Spring Harbor Laboratory.

Ou-Lee, Tsai-Mei et al. "Effect of Increased Temperature in Apical Regions of Maize Ears on Starch-Synthesis Enzymes and Accumulation of Sugars and Starch" *Plant Physiol.*, 1985, pp. 852-855, vol. 79.

Rijven, A.H.G.C. "Heat Inactivation of Starch Synthase in Wheat Endosperm Tissue" *Plant Physiol.*, 1986, pp. 448-453, vol. 81.

Satozawa, T. et al. "Direct Submission", 1995, Accession No. T02965.

Singletary, G. W. et al. "Decreased Starch Synthesis In Heat Stressed Maize Kernels Results From Reduced ADPG-Pyrophosphorylase And Starch Synthase Activities" *Plant Physiol.*, 1993, vol. 102, No. 6(suppl) abstract.

Singletary, G. W. et al. "Heat Stress During Grain Filling in Maize: Effects on Carbohydrate Storage and Metabolism" *Aust. J. Plant Physiol.*, 1994, pp. 829-841, vol. 21.

Smith-White, B. J. et al. "Comparison of Proteins of ADP-Glucose Pyrophosphorylase from Diverse Sources" *J. Mol. Evol.*, 1992, pp. 449-464, vol. 34.

Steel, et al., *Principles and Procedures of Statistics*, Megraw-Hill Book Company, Inc., N.Y., pp. 400-403.

Sowokinos, J. R. et al. "Pyrophosphorylases in *Solanum tuberosum*" *Plant Physiol.*, 1982, pp. 1459-1466, vol. 69.

Thompson, Louis M. "Climatic Change. Weather Variability, and Corn Production" *Agron. J.*, 1986, pp. 649-653, vol. 78.

Tollenaar, M. et al. "Effects Of Temperature On Rate And Duration Of Kernel Dry Matter Accumulation Of Maize" *Can. J. Plant Sci.*, 1988, pp. 935-940, vol. 68.

Villand, P. et al. "ADP-glucose Pyrophosphorylase Large Subunit from Barley Endosperm" *Plant Mol. Biol.*, 1992, Accession No. P30524.

Suzuki, D. T. et al. "Mechanisms of Genetic Change I: Gene Mutation" In *An Introduction to Genetic Analysis*, 4th edition, 1989, pp. 476-499, W. H. Freeman and Company, New York.

Thompson, Louis M. "Weather Variability, Climatic Change, and Grain Production" *Science*, 1975, pp. 535-541, vol. 188.

Bowie et al. "Deciphering the Message in Protein Sequences: Tolerance to Amino Acid Substitutions" *Science*, 1990, pp. 1306-1310, vol. 247.

Ballicora, M. et al. "ADP-Glucose Pyrophosphorylase from Potato Tubers. Site-Directed Mutagenesis Studies of the Regulatory Sites", *Plant. Physiol.*, 1998, pp. 265-274, vol. 118, No. 1.

Ballicora, M. et al. "Heat Stability of the Potato Tuber ADP-Glucose Pyrophosphorylase: Role of Cys Residue 12 in the Small Subunit", *Biochem and Biophys Res Comm*, 1999, pp. 782-786, vol. 257, No. 3.

Ballicora, M. et al. "Construction of Chimeric Enzymes Combining the ADPglucose Pyrophosphorylases from *Escherichia coli* and *Anabaena PCC 7210*", *FASEB Journal*, 2001, p. A203, vol. 15, No. 4.

Ballicora, M. et al., "Construction, expression and characterization of chimeric ADP-glucose pyrophosphorylase made using the potato (*Solanum tuberosum L.*) tuber and cyanobacterial enzymes", *FASEB Journal*, 1999, p. A1533, vol. 13, No. 7.

Giroux, M. et al., "The Large Subunit of the Embryo Isoform of ADP Glucose Pyrosphosphorylase from Maize", *Plant. Physiol.*, 1995, pp. 1333-1334, vol. 103, No. 3.

Cross, J. M. et al. "Both subunits of ADP-Glucose Pyrophosphorylase are regulatory" *Plant Physiology*, May 2004, pp. 137-144, vol. 135, No. 1.

Du Jardin, P. et al. "Isolation and Sequence Analysis of a Complementary DNA Clone Encoding a Subunit of the ADP Glucose Pyrophosphorylase of Potato Tuber Amyloplasts" *Plant Molecular Biology*, 1991, pp. 349-351, vol. 16, No. 2.

Giroux, M. J. et al. "ADP-Glucose Pyrophosphorylase in Shrunken-2 and Brittle-2 Mutants of Maize" *Molecular and General Genetics*, 1994, pp. 400-408, vol. 243, No. 4.

Rudi, H. et al. "A (HIS)6-Tagged Recombinant Barley (*Hordeum vulgare L.*) Endosperm ADP-Glucose Pyrophosphorylase Expressed in the Baculovirus-Insect Cell System in Insensitive to Allosteric Regulation by 3-Phosphoglycerate and Inorganic Phosphate" *FEBS Letters*, Dec. 8, 1997, pp. 124-130, vol. 419, No. 1.

Singh, S. et al. "Expression, Kinetics and Regulatory Properties of Native and Recombinant ADP-Glucose Pyrophosphorylase Isoforms from Chickpea" *Plant Physiology and Biochemistry*, May 2003, pp. 399-405, vol. 41, No. 5.

Cross, J. "ADP-Glucose Pyrophosphorylase Activity From Maize-Potato Mosaics" A Dissertation Presented to the Graduate School of the University of Florida in Partial Fulfillment of the Requirements for the Degree of Doctor of Philosophy, May 16, 2002, pp. i-xiii and 1-112.

Kleczkowski L.A. "Is Leaf ADP-Glucose Pyrophosphorylase an Allosteric Enzyme?" *Biochimica et Biophysica Acta*, 2000, pp. 103-108, vol. 1476.

* cited by examiner

```
   1  ATGGACATGG CTTTGGCGTC TAAAGCCTCC CCTCCGCCAT GGAATGCCAC
  51  CGCCGCCGAG CAGCCAATTC AAAGCGTGA CAAAGCCGCT GCAAATGATT
 101  CAACATACCT CAATCCTCAA GCTCATGATA GTGTTCTTGG AATCATTCTG
 151  GGAGGTGGTG CTGGGACTAG ATTGTACCCC TTGACAAAGA AGCGTGCCAA
 201  GCCTGCAGTG CCATTGGGTG CCAACTATAG ACTGATTGAT ATTCCTGTCA
 251  GCAATTGTCT CAACAGCAAC ATATCCAAGA TCTATGTGCT AACGCAATTT
 301  AACTCTCCTT CCCTCAACCG TCACCTCTCA AGAGCCTACG GGAGCAACAT
 351  TGGAGGGTAC AAGAATGAAG GGTTTGTTGA AGTCTTAGCT GCACAGCAGA
 401  GCCCAGATAA TCCAAACTGG TTTCAGGGTA CTGCAGATGC TGTAAGGCAG
 451  TACTTGTGGT TGTTTGAGGA GCATAATGTG ATGGAATTTC TAATTCTTGC
 501  TGGCGATCAC CTGTACCGGA TGGACTATGA AAAGTTCATT CAGGCACACA
 551  GAGAAACAAA TGCTGATATT ACCGTTGCTG CCCTACCGAT GGATGAGAAG
 601  CGTGCCACTG CATTTGGTCT CATGAAGATT GACGAAGAAG GACGCATTAT
 651  TGAATTTGCA GAGAAACCGC AAGGAGAGCA ATTGCAAGCA ATGAAAGTGG
 701  ATACTACCAT TTAGGTCTT GATGACAAGA GAGCTAAAGA AATGCCTTTC
 751  ATTGCCAGTA TGGGTATATA TGTCATTAGC AAAGACGTGA TGTTAAACCT
 801  ACTTCGTGAC AAGTTCCCTG GGGCCAATGA TTTTGGTAGT GAAGTTATTC
 851  CTGGTGCAAC TTCACTTGGG ATGAGAGTGC AAGCTTATTT ATATGATGGG
 901  TACTGGGAAG ATATTGGTAC CATTGAAGCT TTCTACAATG CCAATTTGGG
 951  CATTACAAAA AAGCCGGTGC CAGATTTTAG CTTTTACGAC CGATCAGCCC
1001  CAATCTACAC CCAACCTCGA TATCTACCAC CATCAAAAAT GCTTGATGCT
1051  GATGTCACAG ATAGTGTCAT TGGTGAAGGT TGTGTGATCA AGAACTGTAA
1101  GATTCATCAT TCCGTGGTTG GACTCAGATC ATGCATATCA GAGGGAGCAA
1151  TTATAGAAGA CTCACTTTTG ATGGGGCAG ATTACTATGA GACTGATGCT
1201  GACAGGAAGT TGCTGGCTGC AAAGGGCAGT GTCCCAATTG GCATCGGCAA
1251  GAATTGTCAC ATTAAAAGAG CCATTATCGA CAAGAATGCC CGTATAGGGG
1301  ACAATGTGAA GATCATTAAC AAAGACAACG TTCAAGAAGC GGCTAGGGAA
1351  ACAGATGGAT ACTTCATCAA GAGTGGGATT GTCACCGTCA TCAAGGATGC
1401  TTTGATTCCA AGTGGAATCA TCATCTGA
```

FIG. 1A

```
  1  MDMALASKAS  PPPWNATAAE  QPIPKRDKAA  ANDSTYLNPQ  AHDSVLGIIL
 51  GGGAGTRLYP  LTKKRAKPAV  PLGANYRLID  IPVSNCLNSN  ISKIYVLTQF
101  NSPSLNRHLS  RAYGSNIGGY  KNEGFVEVLA  AQQSPDNPNW  FQGTADAVRQ
151  YLWLFEEHNV  MEFLILAGDH  LYRMDYEKFI  QAHRETNADI  TVAALPMDEK
201  RATAFGLMKI  DEEGRIIEFA  EKPQGEQLQA  MKVDTTILGL  DDKRAKEMPF
251  IASMGIYVIS  KDVMLNLLRD  KFPGANDFGS  EVIPGATSLG  MRVQAYLYDG
301  YWEDIGTIEA  FYNANLGITK  KPVPDFSFYD  RSAPIYTQPR  YLPPSKMLDA
351  DVTDSVIGEG  CVIKNCKIHH  SVVGLRSCIS  EGAIIEDSLL  MGADYYETDA
401  DRKLLAAKGS  VPIGIGKNCH  IKRAIIDKNA  RIGDNVKIIN  KDNVQEAARE
451  TDGYFIKSGI  VTVIKDALIP  SGIII*
```

FIG. 1B

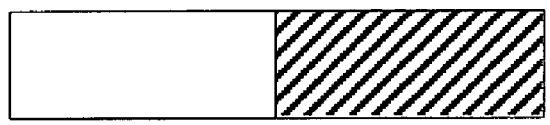

```
IQAHRETNADITVAALPMD EKRATAFGLMKIDEEG
||||||| ||||||||||| ||||||||||||||||
IQAHRETDADITVAALPMD EKRATAFGLMKIDEEG
```

FIG. 2B

VARIANTS OF ADP-GLUCOSE PYROPHOSPHORYLASE AFFECTING PHOSPHATE SENSITIVITY AND OTHER PARAMETERS

CROSS-REFERENCE TO RELATED APPLICATION

This application claims the benefit of U.S. Provisional Application No. 60/338,083, filed Dec. 3, 2001.

This invention was made with government support under National Science Foundation grant number 9982626. The government has certain rights in the invention.

BACKGROUND OF THE INVENTION

The enzyme ADP glucose pyrophosphorylase (AGP) catalyzes the conversion of ATP and α-glucose-1-phosphate to ADP-glucose and pyrophosphate. ADP-glucose is used as a glycosyl donor in starch biosynthesis by plants and in glycogen biosynthesis by bacteria. The importance of ADP-glucose pyrophosphorylase as a key enzyme in the regulation of starch biosynthesis was noted in the study of starch deficient mutants of maize (Zea mays) endosperm (Tsai et al., 1966; Dickinson et al., 1969).

Biochemical and genetic evidence has identified AGP as a key enzyme in starch biosynthesis in higher plants and glycogen biosynthesis in E. coli (Preiss et al., 1994; Preiss et al., 1996). AGP catalyzes what is viewed as the initial step in the starch biosynthetic pathway with the product of the reaction being the activated glucosyl donor, ADPglucose. This is utilized by starch synthase for extension of the polysaccharide polymer (reviewed in Hannah, 1996).

Initial studies with potato AGP showed that expression in E. coli yielded an enzyme with allosteric and kinetic properties very similar to the native tuber enzyme (Iglesias et al., 1993; Ballicora et al., 1995). Greene et al. (1996a; 1996b) showed the usefulness of the bacterial expression system in their structure-function studies with the potato AGP. Multiple mutations important in mapping allosteric and substrate binding sites were identified (Okita et al., 1996).

AGP enzymes have been isolated from both bacteria and plants. Bacterial AGP consists of a homotetramer, while plant AGP from photosynthetic and non-photosynthetic tissues is a heterotetramer composed of two different subunits. The plant enzyme is encoded by two different genes, with one subunit being larger than the other. This feature has been noted in a number of plants. The AGP subunits in spinach leaf have molecular weights of 54 kDa and 51 kDa, as estimated by SDS-PAGE. Both subunits are immunoreactive with antibody raised against purified AGP from spinach leaves (Copeland et al., 1981; Morell et al., 1988). Immunological analysis using antiserum prepared against the small and large subunits of spinach leaf showed that potato tuber AGP is also encoded by two genes (Okita et al., 1990). The cDNA clones of the two subunits of potato tuber (50 and 51 kDa) have also been isolated and sequenced (Muller-Rober et al., 1990; Nakata et al., 1991). The large subunit of potato tuber AGP is heat stable (Nakata et al., supra).

As Hannah and Nelson (Hannah et al, 1975; Hannah et al., 1976) postulated, both Shrunken-2 (Sh2) (Bhave et al., 1990) and Brittle-2 (Bt2) (Bae et al., 1990) are structural genes of maize endosperm ADP-glucose pyrophosphorylase. Sh2 and Bt2 encode the large subunit and small subunit of the enzyme, respectively. From cDNA sequencing, Sh2 and Bt2 proteins have predicted molecular weight of 57,179 Da (Shaw et al., 1992) and 52,224 Da, respectively. The endosperm is the site of most starch deposition during kernel development in maize. Sh2 and bt2 maize endosperm mutants have greatly reduced starch levels corresponding to deficient levels of AGP activity. Mutations of either gene have been shown to reduce AGP activity by about 95% (Tsai et al., supra; Dickinson et al., supra). Furthermore, it has been observed that enzymatic activities increase with the dosage of functional wild type Sh2 and Bt2 alleles, whereas mutant enzymes have altered kinetic properties. AGP is the rate limiting step in starch biosynthesis in plants. Stark et al. (1992) placed a mutant form of E. coli AGP in potato tuber and obtained a 35% increase in starch content.

The cloning and characterization of the genes encoding the AGP enzyme subunits have been reported for various plants. These include Sh2 cDNA (Bhave et al., supra), Sh2 genomic DNA (Shaw et al, supra), and Bt2 cDNA (Bae et al., supra) from maize; small subunit cDNA (Anderson et al., 1989) and genomic DNA (Anderson et al., 1991) from rice; and small and large subunit cDNAs from spinach leaf (Morell et al., supra) and potato tuber (Muller-Rober et al., supra; Nakata et al., supra). In addition, cDNA clones have been isolated from wheat endosperm and leaf tissue (Olive et al., 1989) and Arabidopsis thaliana leaf (Lin et al., 1988). Amino acid sequences of a maize and potato tuber small subunit of AGP, and the nucleotide sequences of the genes that encode them, have been deposited at Genbank under accession numbers AF334959 and X61186, respectively.

AGP functions as an allosteric enzyme in all tissues and organisms investigated to date. The allosteric properties of AGP were first shown to be important in E. coli. A glycogen-overproducing E. coli mutant was isolated and the mutation mapped to the structural gene for AGP, designated as glyC. The mutant E. coli, known as glyC-16, was shown to be more sensitive to the activator, fructose 1,6 bisphosphate, and less sensitive to the inhibitor, cAMP (Preiss, 1984). Although plant AGP's are also allosteric, they respond to different effector molecules than bacterial AGP's. In plants, 3-phosphoglyceric acid (3-PGA) functions as an activator while phosphate ($PO_4$) serves as an inhibitor (Dickinson et al., supra).

BRIEF SUMMARY OF THE INVENTION

The subject invention concerns chimeric AGP subunit proteins and polynucleotides that encode the chimeric proteins. The subject invention provides for mutant AGP enzymes comprising a chimeric subunit of the invention that are less sensitive to inorganic phosphate than wild type AGP enzymes. In one embodiment, the AGP subunit is a small subunit of a plant AGP enzyme.

The subject invention also concerns plants comprising a polynucleotide encoding a chimeric AGP subunit protein of the invention.

The subject invention also concerns methods for producing a plant comprising a polynucleotide of the present invention. Plants produced according to the invention comprise AGP enzymes that are less sensitive to inorganic phosphate than wild type AGP enzyme.

BRIEF DESCRIPTION OF THE DRAWINGS

FIG. 1A shows the nucleotide sequence of a chimeric maize/potato small subunit (MPss) of the invention. Residues 1 to 597 come from the maize endosperm small subunit and residues 598 to 1428 (shown in bold type) come from the potato tuber small subunit.

FIG. 1B shows the amino acid sequence of a chimeric maize/potato small subunit (MPss) encoded by the sequence shown in FIG. 1A. The sequence of amino acid residues 1 to 199 is from maize endosperm small subunit. The sequence of amino acid residues 200 to 475 (shown in bold type) is from potato tuber small subunit.

FIG. 2A shows the chimeric MPss described in FIG. 1B wherein the top and bottom numbers represent the junction location in the maize endosperm sequence or the potato tuber sequence. The chimeric protein consists of the N-terminal 199 residues from maize endosperm (white rectangle) and the C-terminus from potato tuber (hatched rectangle).

FIG. 2B shows the sequence at the junction wherein the arrow points to the junction.

BRIEF DESCRIPTION OF THE SEQUENCES

Figure 3:
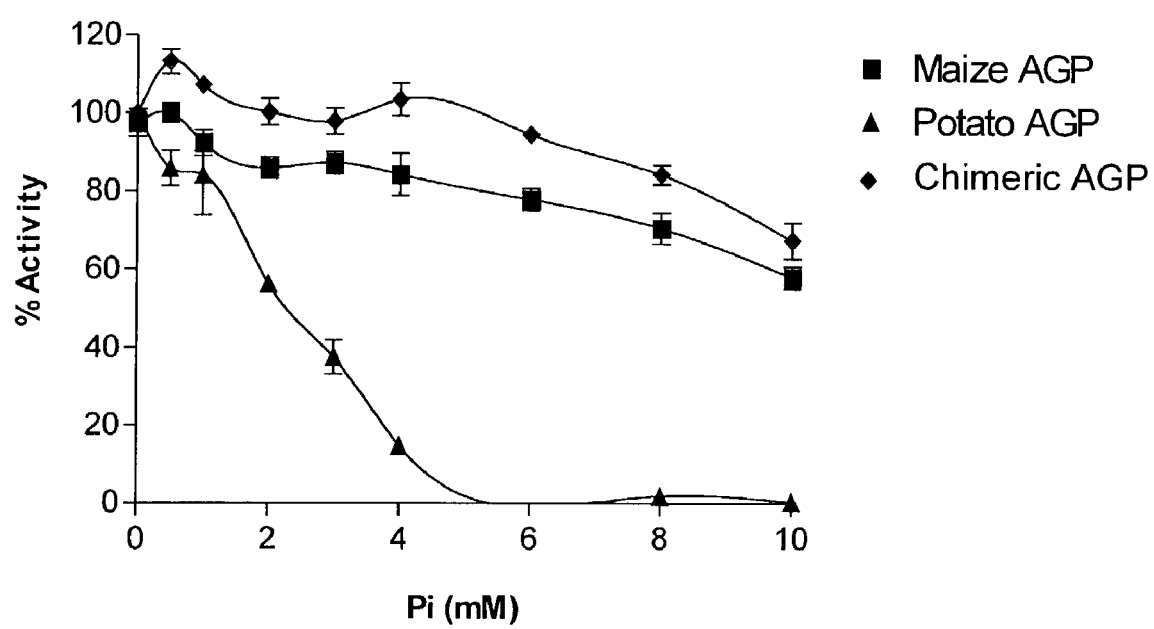
FIG. 3 shows a comparison of activity levels in potato tuber AGP, maize endosperm AGP, and a mutant AGPase comprising a chimeric maize/potato small subunit of the invention and maize wild type large subunit (MPss/MMls). Units represent nM ATP consumed per minute/mg protein.

SEQ ID NO. 1 is the amino acid sequence of an exemplified chimeric AGP small subunit protein of the present invention.

SEQ ID NO. 2 is a nucleotide sequence that encodes an exemplified chimeric AGP small subunit protein of the present invention having the amino acid sequence shown in SEQ ID NO. 1.

SEQ ID NO. 3 is an amino acid sequence of a chimeric AGP small subunit protein of the present invention.

DETAILED DISCLOSURE OF THE INVENTION

The subject invention concerns chimeric AGP subunit proteins and polynucleotides that encode the proteins. In one embodiment, the chimeric AGP subunit comprises portions of AGP small subunit proteins from two or more different plants. When a chimeric small subunit protein of the invention is expressed with a large subunit of AGP, the expressed AGP enzyme is less sensitive to inorganic phosphate than wild type AGP, such as AGP from maize endosperm. Decreased sensitivity to inorganic phosphate of an AGP enzyme in a plant has been associated with changes in certain yield parameters of the plant, such as increased seed weight, increased seed number, etc. The subject invention also concerns AGP enzymes comprising a chimeric subunit of the invention. The non-chimeric subunits of the AGP enzyme can have a wild type sequence or a sequence having one or more mutations, such as a mutation that confers increased seed weight, increased plant biomass, and increased stability to heat stress conditions.

In one embodiment, a chimeric protein of the present invention comprises an N-terminus sequence having approximately the first 150 to 250 amino acids of the N-terminus of a first plant AGP small subunit and a C-terminus sequence comprising approximately the terminal 300 residues or less of the C-terminus of a second plant AGP small subunit. Thus, the C-terminus of the chimeric subunit can comprise the terminal 300, or 299, or 298, or 297, or 296, or 295, and so forth, residues of the C-terminus of the second plant. The subunit sequences can be from an AGP of a monocot or dicot plant, or both a monocot and a dicot. Monocotyledonous plants, such as rice, wheat, barley, oats, sorghum, maize, lilies, and millet are included within the scope of the invention. Dicot plants can include, for example, tobacco, soybean, potato, sweet potato, radish, cabbage, rape, apple tree, and lettuce.

In one embodiment, the first 200 or so amino acids of the N-terminus of the chimeric protein are from the N-terminus of maize endosperm small subunit and the C-terminus amino acids are from the C-terminus of potato tuber small subunit. In a specific embodiment, the C-terminus region of a chimeric protein of the present invention comprises the terminal 276 amino acids of the small subunit of potato tuber. In an exemplified embodiment, the chimeric protein comprises a portion of the small subunit of maize endosperm AGP and a portion of the small subunit of potato tuber AGP. The exemplified protein contains the first 199 amino acids (i.e., amino acids 1 through 199) from the small subunit of maize endosperm AGP and the carboxyl terminal end of the small subunit of potato tuber AGP, starting at amino acid 246 (i.e., amino acids 246 through 521) using the amino acid sequence shown for the protein deposited as Genbank accession number X61186 (or, alternatively, starting at amino acid 175 using the numbering system for the potato AGP subunit as in Hannah et al., 2001). The amino acid sequence of the exemplified chimeric AGP small subunit protein is shown in FIG. 1B. A nucleotide sequence that encodes the exemplified small subunit protein is shown in FIG. 1A. Allelic variants of small subunit protein are also encompassed within the scope of the invention. For example, at amino acid residue 103 of FIG. 1B (SEQ ID NO. 1), the proline can be replaced by an alanine or a threonine amino acid. When expressed in an *E. coli* bacterial expression system, a mutant AGP enzyme comprising the exemplified chimeric small subunit exhibited 16.7 more activity than the standard maize endosperm enzyme expressed in *E. coli*. In the absence of a physiological activator, 3-phosphoglyceric acid (3-PGA), the mutant AGP enzyme exhibited 38.9 times the activity of the standard maize endosperm enzyme.

In those embodiments wherein the chimeric subunit protein comprises plant small subunit sequences and is expressed in conjunction with a non-chimeric large subunit of AGP, then the large subunit can be a large subunit from any plant species. In an exemplified embodiment wherein the chimeric subunit has the amino acid sequence shown in SEQ ID NO. 1 or SEQ ID NO. 3, the large subunit is from maize endosperm AGP.

The subject invention also concerns the polynucleotides that encode the chimeric subunit proteins of the invention. The polynucleotides can comprise nucleotide sequence that only encodes protein, or the polynucleotide can comprise protein coding sequence and non-coding sequences, such as introns found in genomic sequences. Polynucleotides encoding the chimeric subunit proteins of the invention can be prepared using standard techniques known in the art.

Plants (and progeny thereof) and plant tissue bred to contain or transformed with a polynucleotide of the invention, and capable of expressing a chimeric AGP subunit protein of the invention encoded by the polynucleotide, are also contemplated by the present invention. Techniques for transforming plants with a polynucleotide are known in the art and include biolistic bombardment, electroporation, viral-mediated transformation, and *Agrobacterium*-mediated transformation. The plant can be a monocot or a dicot. Monocotyledonous plants, such as rice, wheat, barley, oats, sorghum, maize, lilies, and millet are included within the scope of the invention. In one embodiment, the plant is a cereal plant. Cereal plants contemplated include, for example, maize (*Zea mays*), wheat, barley, and rice. Preferably, the cereal plant is maize. Dicot plants incorporating the subject polynucleotides can include, for example, tobacco, soybean, potato, sweet potato, radish, cabbage, rape, apple tree and lettuce. Plants having a polynucleotide encoding a chimeric protein of the invention can be grown from seeds or plant tissue that comprise the polynucleotide encoding the chimeric protein in their genome.

The subject invention also concerns methods for producing a plant that has a decreased sensitivity to inorganic phosphate, wherein in one embodiment, a polynucleotide of the present invention encoding a chimeric AGP subunit polypeptide is introduced into a plant cell. Techniques for transforming plants with a polynucleotide are known in the art and include biolistic bombardment, electroporation, viral-mediated transformation, and Agrobacterium -mediated transformation. Cells in which the polynucleotide has been incorporated into the genome of the cell can then be propagated and plants or plant tissue obtained therefrom. Plants so obtained can then be propagated or bred with other plants.

Regulatory elements can be used to regulate the expression of a polynucleotide of the invention. These elements can either be regulatory elements that are normally found associated with the coding sequence of an AGP gene (homologous regulatory element) or they can be heterologous regulatory elements. Numerous homologous and heterologous regulatory elements are known in the art and can readily be used to prepare expression constructs for use in the present invention. Transcription initiation regions, for example, can include any of the various opine initiation regions, such as octopine synthase (OCS), mannopine synthase (MAS), and nopaline synthase (NOS) that are found in the Ti plasmids of Agrobacterium tumefaciens. Alternatively, plant viral promoters can also be used, such as the cauliflower mosaic virus (CaMV) 35S or 19S promoter (and including the enhanced CaMV 35S promoter), to control gene expression in a plant. Plant promoters such as prolifera promoter, fruit-specific promoters, Ap3 promoter, heat shock promoters, and seed-specific promoters, such as the promoter from a β-phaseolin gene (of kidney bean) or a glycinin gene (of soybean), and others, can also be used. In one embodiment, regulatory elements used with the present invention direct expression of polynucleotides of the invention specifically in seeds.

Constitutive promoters (such as the CaMV, ubiquitin, actin, or NOS promoter), organ-specific promoters (such as the E8 promoter from tomato), and inducible promoters (such as heat-, light-, hormone-, and chemically-inducible promoters) are contemplated for use with the polynucleotides of the invention. Promoters can be ligated to the protein encoding region of a polynucleotide using standard techniques known in the art. The expression construct may be further optimized by employing supplemental elements such as transcription terminators and/or enhancer elements.

In the construction of heterologous promoter/structural gene combination, the promoter can be positioned about the same distance from the heterologous transcription start site as it is from the transcription start site in its natural genetic environment. As is known in the art, however, some variation in this distance can be accommodated without loss of promoter function.

For expression in plants, the expression construct may optionally contain, in addition to the protein encoding sequence, a plant promoter region, a transcription initiation site and a transcription termination sequence. Unique restriction enzyme sites at the 5' and 3' ends of the expression construct can be included to allow for easy insertion into a preexisting vector. Transcription termination regions that can be used in an expression construct of the invention include, but are not limited to, the octopine synthase or nopaline synthase 3' terminator regions, downstream of the structural gene to provide for efficient termination. The termination region may be obtained from the same gene as the promoter sequence or may be obtained from different genes. DNA sequences which direct polyadenylation of the mRNA encoded by the structure gene are also commonly included in the vector construct.

Expression constructs can also include one or more dominant selectable marker genes, including genes encoding antibiotic resistance and herbicide-resistance for selecting transformed plant cells. Antibiotic-resistance genes can provide for resistance to one or more of the following antibiotics: hygromycin, kanamycin, bleomycin, G418, streptomycin, paromomycin, and spectinomycin. Herbicide-resistance genes can provide for resistance to phosphinothricin acetyltransferase or glyphosate. Other markers used for plant cell transformation screening include genes encoding β-glucuronidase, luciferase, or green fluorescence protein.

Polynucleotides of the present invention can be composed of either RNA or DNA. Preferably, the polynucleotides are composed of DNA. The subject invention also encompasses those polynucleotides that are complementary in sequence to the polynucleotides disclosed herein.

Because of the degeneracy of the genetic code, a variety of different polynucleotide sequences can encode the chimeric AGP subunit proteins of the present invention. In addition, it is well within the skill of a person trained in the art to create alternative polynucleotide sequences encoding the same, or essentially the same, polypeptides of the subject invention. These variant or alternative polynucleotide sequences are within the scope of the subject invention. As used herein, references to "essentially the same" sequence refers to sequences which encode amino acid substitutions, deletions, additions, or insertions which do not materially alter the functional activity of the chimeric subunit proteins described herein.

As used herein, the terms "nucleic acid" and "polynucleotide sequence" refer to a deoxyribonucleotide or ribonucleotide polymer in either single- or double-stranded form, and unless otherwise limited, encompass known analogs of natural nucleotides that can function in a similar manner as naturally-occurring nucleotides. The polynucleotide sequences include both the DNA strand sequence that is transcribed into RNA and the RNA sequence that is translated into protein. The polynucleotide sequences include both full-length sequences as well as shorter sequences derived from the full-length sequences. It is understood that a particular polynucleotide sequence includes the degenerate codons of the native sequence or sequences which may be introduced to provide codon preference in a specific host cell. Allelic variations of the exemplified sequences are also included within the scope of the subject invention. The polynucleotide sequences falling within the scope of the subject invention further include sequences which specifically hybridize with a chimeric sequence of the invention under high stringency conditions. Such hybridization conditions are conventional in the art (see, e.g., Maniatis et al., 1989). The polynucleotide includes both the sense and antisense strands as either individual strands or in the duplex.

Substitution of amino acids other than those specifically exemplified in the chimeric protein disclosed herein are also contemplated within the scope of the present invention. Amino acids can be placed in the following classes: non-polar, uncharged polar, basic, and acidic. Conservative substitutions whereby a chimeric AGP polypeptide having an amino acid of one class is replaced with another amino acid of the same class fall within the scope of the subject invention so long as the polypeptide having the substitution still exhibits less sensitivity to phosphate relative to a wild type polypeptide. Table 1 below provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Substitution of amino acids other than those specifically exemplified or naturally present in an AGP polypeptide are also contemplated within the scope of the present invention. For example, non-natural amino acids can be substituted for the amino acids of the AGP polypeptide, so long as the AGP polypeptide having substituted amino acids retains substantially the same biological activity as the AGP polypeptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

The subject invention also concerns polynucleotides which encode fragments of the a length chimeric subunit protein, so long as those fragments retain substantially the same functional activity as full length protein. The fragments of chimeric subunit protein encoded by these polynucleotides are also within the scope of the present invention.

Polynucleotides and proteins of the subject invention can also be defined in terms of more particular identity and/or similarity ranges with those exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also contemplates those polynucleotide molecules having sequences which are sufficiently homologous with the polynucleotide sequences exemplified herein so as to permit hybridization with that sequence under standard stringent conditions and standard methods (Maniatis et al., supra). As used herein, "stringent" conditions for hybridization refers to conditions wherein hybridization is typically carried out overnight at 20–25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz et al., 1983):

Tm=81.5 C+16.6 Log[Na+]+0.41(%G+C)−0.61(% formamide)−600/length of duplex in base pairs.

Washes are typically carried out as follows:
(1) Twice at room temperature for 15 minutes in 1×SSPE, 0.1% SDS (low stringency wash).
(2) Once at Tm−20 C for 15 minutes in 0.2×SSPE, 0.1% SDS (moderate stringency wash).

The polynucleotide molecules of the subject invention can be used to transform plants to express a mutant AGP enzyme comprising a chimeric subunit polypeptide of the invention in those plants. In addition, the polynucleotides of the subject invention can be used to express recombinant protein.

The chimeric AGP small subunit proteins of the present invention can be expressed in conjunction with the expression of polynucleotides that encode a large subunit of AGP that contains a mutation that has been shown to confer increased seed weight, increased seed number, increased Harvest Index, and/or increased total plant mass, e.g., Rev 6, and/or a mutation(s) that has been shown to confer increased resistance to heat stress (e.g., HS33, HS40, etc.) to a plant expressing an AGP large subunit protein comprising these mutations. See, for example, U.S. Pat. Nos. 5,589,618 and 5,650,557, and published international patent application WO 01/64928 regarding mutations that confer increased seed weight, etc. and U.S. Pat. No. 6,069,300 and published international patent application WO 99/58698 regarding mutations that confer increased resistance to heat stress. Published international patent application WO 01/64928 describes mutations that confer increased total seed number, total plant biomass, etc. Thus, the subject invention also concerns mutant AGP enzymes that comprise a chimeric AGP small subunit polypeptide of the invention and wild type AGP large subunit and/or a mutant AGP large subunit that provides a desirable characteristic or condition, such as increased seed weight and/or heat stability.

All patents, patent applications, provisional applications, and publications referred to or cited herein are incorporated by reference in their entirety to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Expression of AGP Enzymes in *E. coli*

A plasmid containing a nucleotide sequence encoding a small AGP subunit (maize or potato) or a chimeric small subunit of the present invention was transformed into *Escherichia coli* AC70R1-504 containing the wild type Sh2 or potato large AGP subunit coding region on a compatible expression vector (Giroux et al., 1996). AC70R1-504 lacks the endogenous bacterial AGP because of mutation at glgC (Iglesias et al., supra). Bacteria were plated on the medium used by Govons et al. (Govons et al., 1969) except the glucose concentration was reduced to 0.1%.

A 2-ml Luria broth culture containing spectinomycin (100 µg/ml) and kanamycin (75 µg/ml) was inoculated from a glycerol stock of AC70R1-504 E. coli cells expressing wild type or mutant AGP enzyme and grown overnight at 37° C. This culture was used to inoculate a 100-ml culture of Luria broth (100 µg/ml of spectinomycin and 75 µg/ml of kanamycin). The culture was grown to an $OD_{600}$=1.2 and induced for 12 hours by addition of isopropyl β-D-thiogalactoside and nalidixic acid at final concentrations of 0.2 mM and 25 µg/ml, respectively. Cells were harvested as previously described (Greene et al., 1996b, supra). The cell pellet was resuspended at 50 mM Hepes, pH 7.5, 10 mM KPi, pH 7.5, 5 mM $MgCl_2$, 5 mM EDTA, 20% sucrose, and 30% ammonium sulfate. DTT (1 mM), 50 µg/ml of lysozyme, 1 µg/ml of pepstatin, 1 µg/ml of leupeptin, 10 µg/ml of chymostatin, 1 mM phenylmethylsulfonyl fluoride, and 1 mM benzamidine were added just before use. Lysate was sonicated three times for 10 seconds with incubation on ice between steps. Sample was centrifuged for 5 minutes at 12,500 rpm at 4° C., and the supernatant was stored on ice. AGP enzyme activity of crude extract was determined by the pyrophosphorolysis assay (Greene et al., 1996a, supra).

EXAMPLE 2

Preparation and Assay of AGP Enzymes

Table 2 shows 3-PGA activation of various AGP enzymes. "PPss/PPls" represents an AGP enzyme comprising the potato small subunit and potato large subunit. "MMss/MMls" represents an AGP enzyme comprising the maize small subunit and maize large subunit. "MPss/MMls" represents a mutant AGP enzyme comprising the chimeric maize/potato small subunit exemplified herein with a maize large subunit. The numbers in parenthesis in the Ka column represent standard deviations.

TABLE 2

|  | Activation fold | Ka (mM) | Cooperativity |
| --- | --- | --- | --- |
| PPss/PPls | 28 fold | 0.02 (0.008) | H |
| MMss/MMls | 3 to 6 fold | 0.40 (0.06) | H |
| MPss/MMls | 1.2 fold | 3.72 (0.34) | S (ñ = 0.7) |

Table 3 shows phosphate inhibition of PPss/PPls, MPss/MMls, and MMss/MMls AGP enzyme as described for Table 2.

TABLE 3

|  | PPss/PPls | MPss/MMls | MMss/MMls |
| --- | --- | --- | --- |
| Activity without 3-PGA (U) | 0.5 | 292 | 7.5 |
| Activity with 3-PGA (U) | 12.5 | 350 | 21 |

EXAMPLE 3

Adenosine Diphosphate Glucose Pyrophosphorylase Activity from a Chimeric Small Subunit in the Absence of Large Subunit In addition to exhibiting extremely high levels of activity both in the presence and absence of the activator, 3-phosphoglyceric acid, the mosaic small subunit (MPss) of the invention exhibited significant activity when expressed in the absence of a large subunit of AGP.

In one experiment, adenosine diphosphate glucose pyrophosphorylase activity was measured from E. coli cells expressing only a mosaic small subunit of the present invention. The plasmid containing the large subunit of this enzyme was not present. Mutant E. coli cells were grown as described previously except that only kanamycin was present as a selective agent. In addition, E. coli cells expressing both the wild type maize small and large subunits were grown and enzyme activity was extracted from both cultures.

Enzyme assays were performed for 30 minutes at pH 7.5 in the presence of 2 mM glucose-1-P, 1.5 mM ATP, 10 mM 3 PGA. Averaged over two enzyme dilutions, E. coli cells expressing only the mosaic small subunit of the invention had 33% of the activity associated with cells expressing wild type maize AGP (i.e., both large and small wild type subunits). Activity observed was 18,572 and 23,800 cpm for maize wild type and 6,007 and 7,890 cpm from cells containing only the mosaic small subunit.

It should be understood that the examples and embodiments described herein are for illustrative purposes only and that various modifications or changes in light thereof will be suggested to persons skilled in the art and are included within the spirit and purview of this application and the scope of the appended claims.

REFERENCES

U.S. Pat. No. 5,589,618
U.S. Pat. No. 5,650,557
U.S. Pat. No. 6,069,300
WO 01/64928
WO 99/58698
WO 01/64928
Altschul et al. (1990) J. Mol. Biol. 215:402–410.
Altschul et al. (1997) Nucl. Acids Res. 25:3389–3402.
Anderson, J. M., J. Hnilo, R. Larson, T. W. Okita, M. Morell, J. Preiss (1989) "The Encoded Primary Sequence of a Rice Seed ADP-glucose Pyrophosphorylase Subunit and its Homology to the Bacterial Enzyme" J. Biol. Chem. 264:12238–12242.
Anderson, J. M., R. Larson, D. Landencia, W. T. Kim, D. Morrow, T. W. Okita, J. Preiss (1991) "Molecular Characterization of the Gene Encoding a Rice Endosperm-Specific ADPglucose Pyrophosphorylase Subunit and its Developmental Pattern of Transcription" Gene 97:199–205.
Bae, J. M., M. Giroux, L. C. Hannah (1990) "Cloning and Characterization of the Brittle-2 Gene of Maize" Maydica 35:317–322.
Ballicora, M. A., Laughlin, M. J., Fu, Y., Okita, T. W., Barry, G. F., and Preiss, J. (1995) "Adenosine 5'-Diphosphate-Glucose Pyrophosphorylase from Potato Tuber" Plant Physiol. 109:245–251.
Beltz, G. A., K. A. Jacobs, T. H. Eickbush, P. T. Cherbas, and F. C. Kafatos (1983) Methods of Enzymology, R. Wu, L. Grossman and K. Moldave [eds.] Academic Press, New York 100:266–285.
Bhave, M. R., S. Lawrence, C. Barton, L. C. Hannah (1990) "Identification and Molecular Characterization of Shrunken-2 cDNA Clones of Maize" Plant Cell 2:581–588.
Copeland, L., J. Preiss (1981) "Purification of Spinach Leaf ADPglucose Pyrophosphorylase" Plant Physiol. 68:996–1001.

Dickinson, D. B., J. Preiss (1969) "Presence of ADP-glucose Ppyrophosphorylase in Shrunken-2 and Brittle-2 Mutants of Maize Endosperm" *Plant Physiol.* 44:1058–1062.

Giroux, M. J., J. Shaw, G. Barry, G. B. Cobb, T. Greene, T. W. Okita, L. C. Hannah (1996) "A Single Gene Mutation That Increases Maize Seed Weight" *Proc. Natl. Acad. Sci. USA* 93:5824–5829.

Greene, T. W., Chantler, S. E., Kahn, M. L., Barry, G. F., Preiss, J., and Okita, T. W. (1996a) "Mutagenesis of the Potato ADPglucose Pyrophosphorylase and Characterization of an Allosteric Mutant Defective in 3-phosphoglycerate Activation" *Proc. Natl. Acad. Sci.* 93:1509–1513.

Greene, T. W., Woodbury, R. L., and Okita, T. W. (1996b) "Aspartic Acid 413 is Important for the Normal Allosteric Functioning of ADP-Glucose Pyrophosphorylase" *Plant Physiol.* 112:1315–1320.

Govons, S., R. Vinopal, J. Ingraham, J. Preiss (1969) "Isolation of Mutants of *Escherichia coli* B Altered in Their Ability to Synthesize Glycogen" *J. Bacteriol.* 97:970–972.

Hannah, L. C., O. E. Nelson (1975) "Characterization of Adenosine Diphosphate Glucose Pyrophosphorylase From Developing Maize Seeds" *Plant Physiol.* 55:297–302.

Hannah, L. C., and Nelson, Jr., O. E. (1976) "Characterization of Adenosine Diphosphate Glucose Pyrophosphorylase From Shrunken-2 and Brittle-2 Mutants of Maize" *Biochem. Genet.* 14:547–560.

Hannah, L. Curtis (1997) "Starch Synthesis in the Maize Seed" In: *Cellular and Molecular Biology of Plant Seed Development*, B. A. Larkins and I. K. Vasil (eds.), Kluwer Academic Publishers, Dordrecht, The Netherlands, 4:375–405.

Hannah L. C., Shaw, J. R., Giroux, M., Reyss, A., Prioul, J.-L., Bae, J.-M. and Lee, J.-Y. (2001) "Maize Genes Encoding the Small Subunit of ADP-Glucose Pyrophosphorylase" *Plant Physiol.* 127:173–183.

Iglesias, A., Barry, G. F., Meyer, C., Bloksberg, L., Nakata, P., Greene, T., Laughlin, M. J., Okita, T. W., Kishore, G. M., and Preiss, J. (1993) "Expression of the Potato Tuber ADP-glucose Pyrophosphorylase in *Escherichia coli*" *J. Biol Chem.* 268:1081–1086.

Karlin and Altschul (1990) *Proc. Natl. Acad. Sci. USA* 87:2264–2268.

Karlin and Altschul (1993) *Proc. Natl. Acad. Sci. USA* 90:5873–5877.

Lin, T., Caspar, T., Sommerville, C. R., and Preiss, J. (1988) "A Starch Deficient Mutant of *Arabidopsis thaliana* with Low ADPglucose Pyrophosphorylase Activity Lacks One of the Two Subunits of the Enzyme" *Plant Physiol.* 88:1175–1181.

Maniatis, T. et al. (1982) "Nuclease Bal31" In *Enzymes Used in Molecular Cloning, A Laboratory Manual*, pp. 135–139, Cold Spring Harbor Laboratory, Cold Spring Harbor, N.Y.

Maniatis, T., E. F. Fritsch, J. Sambrook (1989) *Molecular Cloning: A Laboratory Manual*, 2nd Edition, Cold Spring Harbor Laboratory, Cold Spring Harbor, N.Y.

Morell, M., M. Bloon, V. Knowles, J. Preiss (1988) "Affinity Labeling of the Allosteric Activator Site(s) of Spinach Leaf ADP-glucose pyrophosphorylase" *J. Bio. Chem.* 263(2):633–637.

Muller-Rober, B. T., J. Kossmann, L. C. Hannah, L. Willmitzer, U. Sounewald (1990) "One of the Two Different ADP-glucose Pyrophosphorylase Genes from Potato Responds Strongly to Elevated Levels of Sucrose" *Mol. Gen. Genet.* 224:136–146.

Nakata, P. A., T. W. Greene, J. M. Anderson, B. J. Smith-White, T. W. Okita, J. Preiss (1991) "Comparison of Primary Sequences of Two Potato Tuber ADP-glucose Pyrophosphorylase Subunits" *Plant Mol. Biol.* 17:1089–1093.

Okita, T. W., Nakata, P. A., Anderson, J. M., Sowokinos, J., Morell, J., and Preiss, J. (1990) "The Subunit Structure of Potato Tuber ADPglucose Pyrophosphorylase" *Plant Physiol.* 93:785–790.

Okita, T. W., Greene, T. W., Laughlin, M. J., Salamone, P., Woodbury, R., Choi, S., Ito, H., Kavakli, H., and Stephens, K. (1996) "Engineering Plant Starches by the Generation of Modified Plant Biosynthetic Enzymes," In *Engineering Crops for Industrial End Uses*, Shewry, P. R., Napier, J. A., and Davis, P., eds., Portland Press Ltd., London.

Olive, M. R., R. J. Ellis, W. W. Schuch (1989) "Isolation and Nucleotide Sequences of cDNA Clones Encoding ADP-glucose Pyrophosphorylase Polypeptides from Wheat Leaf and Endoosperm" *Plant Physiol. Mol. Biol.* 12:525–538.

Preiss, J. (1984) "Bacterial Glycogen Synthesis and Its Regulation" *Ann. Rev. Microbiol.* 38:419–458.

Preiss, J. and Romeo, T. (1994) "Molecular Biology and Regulatory Aspects of Glycogen Biosynthesis in Bacteria" *Progress in Nuc. Acid Res. and Mol Biol.* 47:299–329.

Preiss, J. and Sivak, M. (1996) "Starch Synthesis in Sinks and Sources" In *Photoassimilate distribution in plants and crops: source-sink relationships.* Zamski, E., ed., Marcil Dekker Inc., pp. 1–63.

Shaw, J. R., L. C. Hannah (1992) "Genomic Nucleotide Sequence of a Wild-Type Shrunken-2 Allele of *Zea mays*" *Plant Physiol.* 98:1214–1216.

Stark, D. M. et al. (1992) "Regulation of the Amount of Starch in Plant Tissues by ADP Glucose Pyrophosphorylase" *Science* 258:287–292.

Tsai, C. Y., and Nelson, Jr., O. E. (1966) "Starch-Deficient Maize Mutant Lacking Adenosine Diphosphate Glucose Pyrophosphorylase Activity" *Science* 151:341–343.

We claim:

1. A polynucleotide encoding a chimeric ADP glucose pyrophosphorylase (AGP) subunit protein that, when expressed with a large subunit of AGP to form an AGP enzyme, said AGP enzyme exhibits decreased sensitivity to inorganic phosphate relative to wildtype maize endosperm AGP enzyme, wherein said chimeric protein comprises an N-terminus sequence that comprises the first 150 to 250 amino acids of the N-terminus region of a maize endosperm AGP small subunit protein and a C-terminus sequence that comprises the terminal 275 to 300 residues of the C-terminus region of a potato tuber AGP small subunit protein.

2. The polynucleotide according to claim 1, wherein said polynucleotide encodes a protein having the amino acid sequence shown in SEQ ID NO. 1 or SEQ ID NO. 3.

3. The polynucleotide according to claim 1, wherein said polynucleotide comprises the nucleotide sequence shown in SEQ ID NO. 2.

4. A transgenic plant, plant tissue, or seed comprising a polynucleotide encoding a chimeric ADP glucose pyrophosphorylase (AGP) subunit protein that, when expressed with a large subunit of AGP to form an AGP enzyme, said AGP enzyme exhibits decreased sensitivity to inorganic phosphate relative to wildtype maize endosperm AGP enzyme, wherein said chimeric protein comprises an N-terminus sequence that comprises the first 150 to 250 amino acids of the N-terminus region of a maize endosperm AGP small subunit protein and a C-terminus sequence that comprises the terminal 275 to 300 residues of the C-terminus region of a potato tuber AGP small subunit protein.

5. The plant, plant tissue, or seed according to claim 4, wherein said polynucleotide encodes a protein having the amino acid sequence shown in SEQ ID NO. 1 or SEQ ID NO. 3.

6. The plant, plant tissue, or seed according to claim 4, wherein said polynucleotide comprises the nucleotide sequence shown in SEQ ID NO. 2.

7. The plant, plant tissue, or seed according to claim 5, wherein said plant also expresses the maize large subunit of AGP.

8. A method for decreasing the sensitivity of AGP enzymes in a plant to inorganic phosphate, comprising introducing into a plant a polynucleotide encoding a chimeric ADP glucose pyrophosphorylase (AGP) subunit protein that, when expressed with a large subunit of AGP to form an AGP enzyme, said AGP enzyme exhibits decreased sensitivity to inorganic phosphate relative to wildtype maize endosperm AGP enzyme, wherein said chimeric protein comprises an N-terminus sequence that comprises the first 150 to 250 amino acids of the N-terminus region of a maize endosperm AGP small subunit protein and a C-terminus sequence that comprises the terminal 275 to 300 residues of the C-terminus region of a potato tuber AGP small subunit protein.

9. The method according to claim 8, wherein said polynucleotide encodes a protein having the amino acid sequence shown in SEQ ID NO. 1 or SEQ ID NO. 3.

10. The method according to claim 8, wherein said polynucleotide comprises the nucleotide sequence shown in SEQ ID NO. 2.

11. The method according to claim 9, wherein said plant also expresses the maize large subunit of AGP.

12. The plant, plant tissue, or seed according to claim 4, wherein said plant, plant tissue, or seed is a monocot.

13. The plant, plant tissue, or seed according to claim 12, wherein said monocot is selected from the group consisting of rice, wheat, barley, oats, sorghum, maize, lilies, and millet.

14. The plant, plant tissue, or seed according to claim 12, wherein said monocot is a cereal.

15. The plant, plant tissue, or seed according to claim 12, wherein said monocot is maize.

16. The plant, plant tissue, or seed according to claim 4, wherein said plant, plant tissue, or seed is a dicot.

17. The plant, plant tissue, or seed according to claim 16, wherein said dicot is selected from the group consisting of soybean, tobacco, potato, sweet potato, radish, cabbage, rape, apple tree, and lettuce.

18. The plant, plant tissue, or seed according to claim 7, wherein said large subunit of AGP comprises a mutation.

19. The plant, plant tissue, or seed according to claim 18, wherein said mutation confers increased individual seed weight on said plant.

20. The plant, plant tissue, or seed according to claim 18, wherein said mutation is the Rev6 mutation.

21. The plant, plant tissue, or seed according to claim 18, wherein said mutation confers increased resistance to heat stress conditions on said plant.

22. The plant, plant tissue, or seed according to claim 18, wherein said mutation is the HS 33 mutation.

23. The method according to claim 8, wherein said plant is a monocot.

24. The method according to claim 23, wherein said monocot plant is selected from the group consisting of rice, wheat, barley, oats, sorghum, maize, lilies, and millet.

25. The method according to claim 23, wherein said monocot plant is a cereal plant.

26. The method according to claim 23, wherein said monocot plant is maize.

27. The method according to claim 8, wherein said plant is a dicot.

28. The method according to claim 27, wherein said dicot plant is selected from the group consisting of soybean, tobacco, potato, sweet potato, radish, cabbage, rape, apple tree, and lettuce.

29. The method according to claim 11, wherein said large subunit of AGP comprises a mutation.

30. The method according to claim 29, wherein said mutation is the Rev6 mutation.

31. The method according to claim 29, wherein said mutation confers increased individual seed weight on said plant.

32. The method according to claim 29, wherein said mutation confers increased resistance to heat stress conditions on said plant.

33. The method according to claim 29, wherein said mutation is the HS 33 mutation.

34. A cell comprising a polynucleotide according to claim 1.

35. The cell according to claim 34, wherein said polynucleotide encodes a protein having the amino acid sequence shown in SEQ ID NO. 1 or SEQ ID NO. 3.

36. The cell according to claim 34, wherein said polynucleotide comprises the nucleotide sequence shown in SEQ ID NO. 2.

37. The cell according to claim 34, wherein said cell also expresses the maize large subunit of AGP.

38. The cell according to claim 37, wherein said large subunit of AGP comprises a mutation.

39. The cell according to claim 38, wherein said mutation is the Rev6 mutation.

40. The cell according to claim 38, wherein said mutation confers increased individual seed weight on said plant.

41. The cell according to claim 38, wherein said mutation confers increased resistance to heat stress conditions on said plant.

42. The cell according to claim 38, wherein said mutation is the HS 33 mutation.

43. The cell according to claim 34, wherein said cell is a monocot plant cell.

44. The cell according to claim 43, wherein said monocot cell is selected from the group consisting of rice, wheat, barley, oats, sorghum, maize, lilies, and millet.

45. The cell according to claim 43, wherein said monocot cell is a cereal plant.

46. The cell according to claim 43, wherein said monocot cell is maize.

47. The cell according to claim 34, wherein said cell is a dicot plant cell.

48. The cell according to claim 47, wherein said dicot cell is selected from the group consisting of soybean, tobacco, potato, sweet potato, radish, cabbage, rape, apple tree, and lettuce.

49. An expression construct comprising a polynucleotide according to claim 1.

50. The expression construct according to claim 49, wherein said expression construct comprises one or more regulatory elements selected from the group consisting of a promoter sequence, a transcription initiation site, and a transcription termination sequence.

51. The expression construct according to claim 49, wherein said polynucleotide encodes a protein having the amino acid sequence shown in SEQ ID NO. 1 or SEQ ID NO. 3.

52. The expression construct according to claim 49, wherein said polynucleotide comprises the nucleotide sequence shown in SEQ ID NO. 2.

53. The expression construct according to claim 50, wherein said promoter is a seed-specific promoter, a tissue-specific promoter, a fruit-specific promoter, a constitutive promoter, or an inducible promoter.

54. The expression construct according to claim 53, wherein said seed-specific promoter is a β-phaseolin gene promoter or a glycinin gene promoter.

55. The expression construct according to claim 53, wherein said constitutive promoter is a CaMV promoter, ubiquitin promoter, actin promoter, or nopaline synthase (NOS) promoter.

56. The expression construct according to claim 53, wherein said tissue-specific promoter is an E8 promoter.

57. The expression construct according to claim 50, wherein said promoter is selected from the group consisting of an octopine synthase (OCS) promoter, a mannopine synthase (MAS) promoter, a nopaline synthase (NOS) promoter, a CaMV 35S promoter, a CaMV 19S promoter, a prolifera promoter, an Ap3 promoter, and a heat shock promoter.

58. A method for producing a plant having an AGP enzyme that exhibits decreased sensitivity to inorganic phosphate, said method comprising:
a) introducing a polynucleotide as defined in claim 1 into a plant cell and growing a plant from said plant cell; or
b) breeding a plant comprising a polynucleotide as defined in claim 1 with another plant of the same species and obtaining progeny that comprise said polynucleotide.

* * * * *

SEQUENCE LISTING

```
<160> NUMBER OF SEQ ID NOS: 3

<210> SEQ ID NO 1
<211> LENGTH: 475
<212> TYPE: PRT
<213> ORGANISM: Artificial Sequence
<220> FEATURE:
<223> OTHER INFORMATION: Amino acid sequence of a chimeric AGP small
      subunit protein
```

```
<400> SEQUENCE: 1

Met Asp Met Ala Leu Ala Ser Lys Ala Ser Pro Pro Trp Asn Ala
1               5                   10                  15

Thr Ala Ala Glu Gln Pro Ile Pro Lys Arg Asp Lys Ala Ala Asn
            20                  25                  30

Asp Ser Thr Tyr Leu Asn Pro Gln Ala His Asp Ser Val Leu Gly Ile
        35                  40                  45

Ile Leu Gly Gly Gly Ala Gly Thr Arg Leu Tyr Pro Leu Thr Lys Lys
    50                  55                  60

Arg Ala Lys Pro Ala Val Pro Leu Gly Ala Asn Tyr Arg Leu Ile Asp
65                  70                  75                  80

Ile Pro Val Ser Asn Cys Leu Asn Ser Asn Ile Ser Lys Ile Tyr Val
                85                  90                  95

Leu Thr Gln Phe Asn Ser Pro Ser Leu Asn Arg His Leu Ser Arg Ala
                100                 105                 110

Tyr Gly Ser Asn Ile Gly Gly Tyr Lys Asn Glu Gly Phe Val Glu Val
                115                 120                 125

Leu Ala Ala Gln Gln Ser Pro Asp Asn Pro Asn Trp Phe Gln Gly Thr
130                 135                 140

Ala Asp Ala Val Arg Gln Tyr Leu Trp Leu Phe Glu Glu His Asn Val
145                 150                 155                 160

Met Glu Phe Leu Ile Leu Ala Gly Asp His Leu Tyr Arg Met Asp Tyr
                165                 170                 175

Glu Lys Phe Ile Gln Ala His Arg Glu Thr Asn Ala Asp Ile Thr Val
                180                 185                 190

Ala Ala Leu Pro Met Asp Glu Lys Arg Ala Thr Ala Phe Gly Leu Met
                195                 200                 205

Lys Ile Asp Glu Glu Gly Arg Ile Ile Glu Phe Ala Glu Lys Pro Gln
            210                 215                 220

Gly Glu Gln Leu Gln Ala Met Lys Val Asp Thr Thr Ile Leu Gly Leu
225                 230                 235                 240

Asp Asp Lys Arg Ala Lys Glu Met Pro Phe Ile Ala Ser Met Gly Ile
                245                 250                 255

Tyr Val Ile Ser Lys Asp Val Met Leu Asn Leu Leu Arg Asp Lys Phe
                260                 265                 270

Pro Gly Ala Asn Asp Phe Gly Ser Glu Val Ile Pro Gly Ala Thr Ser
                275                 280                 285

Leu Gly Met Arg Val Gln Ala Tyr Leu Tyr Asp Gly Tyr Trp Glu Asp
                290                 295                 300

Ile Gly Thr Ile Glu Ala Phe Tyr Asn Ala Asn Leu Gly Ile Thr Lys
305                 310                 315                 320

Lys Pro Val Pro Asp Phe Ser Phe Tyr Asp Arg Ser Ala Pro Ile Tyr
                325                 330                 335

Thr Gln Pro Arg Tyr Leu Pro Pro Ser Lys Met Leu Asp Ala Asp Val
                340                 345                 350

Thr Asp Ser Val Ile Gly Glu Gly Cys Val Ile Lys Asn Cys Lys Ile
                355                 360                 365

His His Ser Val Val Gly Leu Arg Ser Cys Ile Ser Glu Gly Ala Ile
                370                 375                 380

Ile Glu Asp Ser Leu Leu Met Gly Ala Asp Tyr Tyr Glu Thr Asp Ala
385                 390                 395                 400

Asp Arg Lys Leu Leu Ala Ala Lys Gly Ser Val Pro Ile Gly Ile Gly
                405                 410                 415
```

```
Lys Asn Cys His Ile Lys Arg Ala Ile Ile Asp Lys Asn Ala Arg Ile
            420                 425                 430

Gly Asp Asn Val Lys Ile Ile Asn Lys Asp Asn Val Gln Glu Ala Ala
        435                 440                 445

Arg Glu Thr Asp Gly Tyr Phe Ile Lys Ser Gly Ile Val Thr Val Ile
    450                 455                 460

Lys Asp Ala Leu Ile Pro Ser Gly Ile Ile Ile
465                 470                 475
```

<210> SEQ ID NO 2
<211> LENGTH: 1428
<212> TYPE: DNA
<213> ORGANISM: Artificial Sequence
<220> FEATURE:
<223> OTHER INFORMATION: Nucleotide sequence encoding a chimeric AGP
    small subunit protein having the amino acid sequence shown in
    SEQ ID NO. 1

<400> SEQUENCE: 2

```
atggacatgg ctttggcgtc taaagcctcc cctccgccat ggaatgccac cgccgccgag      60
cagccaattc caaagcgtga caaagccgct gcaaatgatt caacatacct caatcctcaa     120
gctcatgata gtgttcttgg aatcattctg ggaggtggtg ctgggactag attgtacccc     180
ttgacaaaga agcgtgccaa gcctgcagtg ccattgggtg ccaactatag actgattgat     240
attcctgtca gcaattgtct caacagcaac atatccaaga tctatgtgct aacgcaattt     300
aactctcctt ccctcaaccg tcacctctca agagcctacg ggagcaacat tggagggtac     360
aagaatgaag ggtttgttga agtcttagct gcacagcaga gcccagataa tccaaactgg     420
tttcaggggta ctgcagatgc tgtaaggcag tacttgtggt tgtttgagga gcataatgtg     480
atggaatttc taattcttgc tggcgatcac ctgtaccgga tggactatga aaagttcatt     540
caggcacaca gagaaacaaa tgctgatatt accgttgctg ccctaccgat ggatgagaag     600
cgtgccactg catttggtct catgaagatt gacgaagaag acgcattat tgaatttgca     660
gagaaaccgc aaggagagca attgcaagca atgaaagtgg atactaccat tttaggtctt     720
gatgacaaga gagctaaaga aatgccttc attgccagta tgggtatata tgtcattagc     780
aaagacgtga tgttaaacct acttcgtgac aagttccctg gggccaatga ttttggtagt     840
gaagttattc ctggtgcaac ttcacttggg atgagagtgc aagcttattt atatgatggg     900
tactgggaag atattggtac cattgaagct ttctacaatg ccaatttggg cattacaaaa     960
aagccggtgc cagatttag ctttacgac cgatcagccc caatctacac ccaacctcga    1020
tatctaccac catcaaaaat gcttgatgct gatgtcacag atagtgtcat tggtgaaggt    1080
tgtgtgatca agaactgtaa gattcatcat tccgtggttg gactcagatc atgcatatca    1140
gagggagcaa ttatagaaga ctcacttttg atgggggcag attactatga gactgatgct    1200
gacaggaagt tgctggctgc aaagggcagt gtcccaattg gcatcggcaa gaattgtcac    1260
attaaaagag ccattatcga caagaatgcc cgtataggg acaatgtgaa gatcattaac    1320
aaagacaacg ttcaagaagc ggctagggaa acagatggat acttcatcaa gagtgggatt    1380
gtcaccgtca tcaaggatgc tttgattcca agtggaatca tcatctga                1428
```

<210> SEQ ID NO 3
<211> LENGTH: 475
<212> TYPE: PRT
<213> ORGANISM: Artificial Sequence
<220> FEATURE:
<223> OTHER INFORMATION: Amino acid sequence of a chimeric AGP small subunit protein

<400> SEQUENCE: 3

```
Met Asp Met Ala Leu Ala Ser Lys Ala Ser Pro Pro Trp Asn Ala
1               5                   10                  15

Thr Ala Glu Gln Pro Ile Pro Lys Arg Asp Lys Ala Ala Ala Asn
                20                  25                  30

Asp Ser Thr Tyr Leu Asn Pro Gln Ala His Asp Ser Val Leu Gly Ile
            35                  40                  45

Ile Leu Gly Gly Gly Ala Gly Thr Arg Leu Tyr Pro Leu Thr Lys Lys
    50                  55                  60

Arg Ala Lys Pro Ala Val Pro Leu Gly Ala Asn Tyr Arg Leu Ile Asp
65                  70                  75                  80

Ile Pro Val Ser Asn Cys Leu Asn Ser Asn Ile Ser Lys Ile Tyr Val
                85                  90                  95

Leu Thr Gln Phe Asn Ser Ala Ser Leu Asn Arg His Leu Ser Arg Ala
                100                 105                 110

Tyr Gly Ser Asn Ile Gly Gly Tyr Lys Asn Glu Gly Phe Val Glu Val
            115                 120                 125

Leu Ala Ala Gln Gln Ser Pro Asp Asn Pro Asn Trp Phe Gln Gly Thr
130                 135                 140

Ala Asp Ala Val Arg Gln Tyr Leu Trp Leu Phe Glu Glu His Asn Val
145                 150                 155                 160

Met Glu Phe Leu Ile Leu Ala Gly Asp His Leu Tyr Arg Met Asp Tyr
                165                 170                 175

Glu Lys Phe Ile Gln Ala His Arg Glu Thr Asn Ala Asp Ile Thr Val
            180                 185                 190

Ala Ala Leu Pro Met Asp Glu Lys Arg Ala Thr Ala Phe Gly Leu Met
            195                 200                 205

Lys Ile Asp Glu Glu Gly Arg Ile Ile Glu Phe Ala Glu Lys Pro Gln
210                 215                 220

Gly Glu Gln Leu Gln Ala Met Lys Val Asp Thr Thr Ile Leu Gly Leu
225                 230                 235                 240

Asp Asp Lys Arg Ala Lys Glu Met Pro Phe Ile Ala Ser Met Gly Ile
                245                 250                 255

Tyr Val Ile Ser Lys Asp Val Met Leu Asn Leu Leu Arg Asp Lys Phe
            260                 265                 270

Pro Gly Ala Asn Asp Phe Gly Ser Glu Val Ile Pro Gly Ala Thr Ser
        275                 280                 285

Leu Gly Met Arg Val Gln Ala Tyr Leu Tyr Asp Gly Tyr Trp Glu Asp
    290                 295                 300

Ile Gly Thr Ile Glu Ala Phe Tyr Asn Ala Asn Leu Gly Ile Thr Lys
305                 310                 315                 320

Lys Pro Val Pro Asp Phe Ser Phe Tyr Asp Arg Ser Ala Pro Ile Tyr
                325                 330                 335

Thr Gln Pro Arg Tyr Leu Pro Pro Ser Lys Met Leu Asp Ala Asp Val
            340                 345                 350

Thr Asp Ser Val Ile Gly Glu Gly Cys Val Ile Lys Asn Cys Lys Ile
        355                 360                 365

His His Ser Val Val Gly Leu Arg Ser Cys Ile Ser Glu Gly Ala Ile
    370                 375                 380
```

-continued

```
Ile Glu Asp Ser Leu Leu Met Gly Ala Asp Tyr Tyr Glu Thr Asp Ala
385                 390                 395                 400

Asp Arg Lys Leu Leu Ala Ala Lys Gly Ser Val Pro Ile Gly Ile Gly
            405                 410                 415

Lys Asn Cys His Ile Lys Arg Ala Ile Ile Asp Lys Asn Ala Arg Ile
            420                 425                 430

Gly Asp Asn Val Lys Ile Ile Asn Lys Asp Asn Val Gln Glu Ala Ala
            435                 440                 445

Arg Glu Thr Asp Gly Tyr Phe Ile Lys Ser Gly Ile Val Thr Val Ile
        450                 455                 460

Lys Asp Ala Leu Ile Pro Ser Gly Ile Ile Ile
465                 470                 475
```